United States Patent
Kawahara et al.

(10) Patent No.: US 7,427,282 B2
(45) Date of Patent: Sep. 23, 2008

(54) HIGH-FREQUENCY CUTTING INSTRUMENT FOR ENDOSCOPE

(75) Inventors: Yoshiro Kawahara, Okayama (JP); Hiroaki Shibata, Saitama (JP)

(73) Assignee: Hoya Corporation, Tokyo (JP)

( * ) Notice: Subject to any disclaimer, the term of this patent is extended or adjusted under 35 U.S.C. 154(b) by 288 days.

(21) Appl. No.: 11/134,357

(22) Filed: May 23, 2005

(65) Prior Publication Data

US 2005/0261675 A1 Nov. 24, 2005

(30) Foreign Application Priority Data

May 24, 2004 (JP) ............................. 2004-152632

(51) Int. Cl.
*A61B 18/14* (2006.01)
(52) U.S. Cl. ........................................ 606/45; 606/46
(58) Field of Classification Search ............... 606/41, 606/45–47
See application file for complete search history.

(56) References Cited

U.S. PATENT DOCUMENTS

| | | | |
|---|---|---|---|
| 3,910,279 A * | 10/1975 | Okada et al. | 606/47 |
| 5,643,294 A * | 7/1997 | Tovey et al. | 606/148 |
| 6,152,922 A | 11/2000 | Ouchi | |
| 6,190,384 B1 | 2/2001 | Ouchi | |
| 6,514,248 B1 * | 2/2003 | Eggers et al. | 606/41 |
| 2005/0049454 A1 | 3/2005 | Ouchi | |

FOREIGN PATENT DOCUMENTS

| | | |
|---|---|---|
| JP | 61-007694 | 3/1986 |
| JP | 10-179603 | 7/1998 |
| JP | 2001-079017 | 3/2001 |

OTHER PUBLICATIONS

English language Abstract of JP 10-179603.
English language Abstract of JP 2001-079017.
U.S. Appl. No. 11/086,436, filed Mar. 23, 2005, Ouchi.

* cited by examiner

*Primary Examiner*—Lee S Cohen
(74) *Attorney, Agent, or Firm*—Greenblum & Bernstein, P.L.C.

(57) ABSTRACT

A high-frequency cutting instrument for an endoscope is provided. The instrument is provided with a flexible sheath formed of insulating material, a high-frequency electrode placed to be exposed on a lateral part of the flexible sheath in the vicinity of a tip of the flexible sheath, and a conductive wire inserted into the flexible sheath and electrically connected to the high-frequency electrode. In this structure, the flexible sheath is separated into a distal sheath and a proximal sheath at a separating position along the flexible sheath. The distal sheath and the proximal sheath are connected together at the separating position to be rotatable relative to each other around an axis line of the flexible sheath. Further, the distal sheath is rotated relative to the proximal sheath around the axis line by rotating the conductive wire around the axis line at a proximal end of the proximal sheath.

12 Claims, 6 Drawing Sheets

HIGH-FREQUENCY CUTTING INSTRUMENT FOR ENDOSCOPE

INCORPORATION BY REFERENCE

This application claims priority of Japanese Patent Application No. 2004-152632, filed on May 24, 2004, the entire subject matter of the applications is incorporated herein by reference thereto.

BACKGROUND OF THE INVENTION

The present invention relates to a high-frequency cutting instrument for an endoscope, to be inserted into an instrument-inserting channel of an endoscope and used for surgical operations such as endoscopic mucosal resection (EMR).

High-frequency cutting instruments are widely used today for performing surgical operations (endoscopic mucosal resection, etc.) safely and precisely. For example, in an operative procedure for the endoscopic mucosal resection, physiological saline is injected under a mucous membrane of a body part as the target of resection so as to bulge the part with the saline, and the bulged part is horizontally incised and resected at its base with a high-frequency cutting instrument for an endoscope (inserted into the endoscope). For such purposes, high-frequency cutting instruments for endoscopes, having a high-frequency electrode exposed on a lateral part of an electrically insulating flexible sheath in the vicinity of the tip of the sheath, are suitable. An example of such a high-frequency cutting instrument is disclosed in Japanese Utility Model Publication No. SHO 61-7694.

Figure 6:
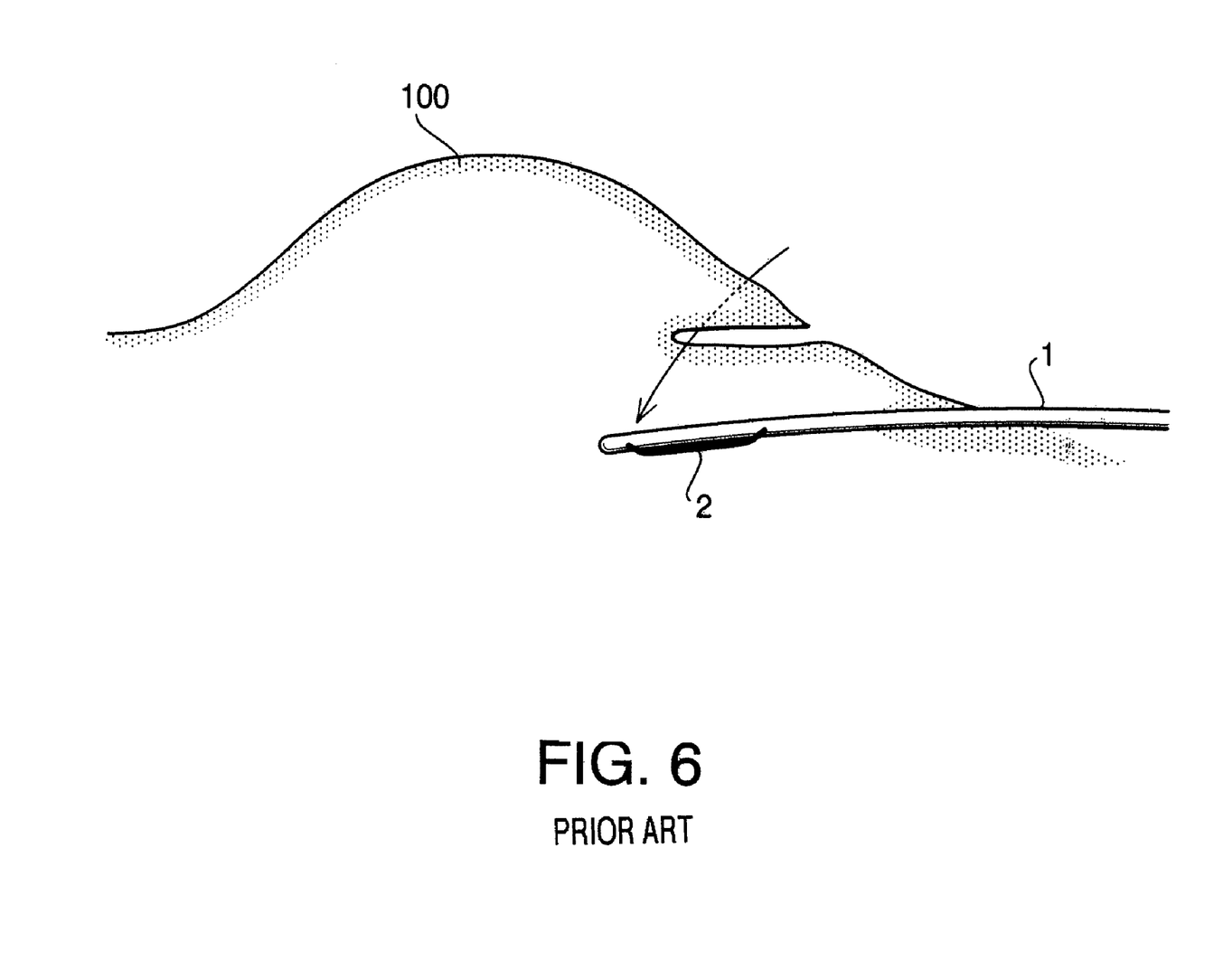
FIG. 6 is a schematic diagram showing mucosal resection treatment employing a conventional high-frequency cutting instrument.

FIG. 6 is a schematic diagram showing a procedure for the endoscopic mucosal resection employing a conventional high-frequency cutting instrument for an endoscope like the one shown in the above Utility Model Publication. In the procedure, the tip of a flexible sheath 1 protruding from an instrument-inserting channel of an unshown endoscope is moved horizontally by operating the endoscope, by which a bulged part 100 is cut off at its base with a high-frequency electrode 2 placed in the vicinity of the tip of the flexible sheath 1 and energized with high-frequency current.

However, when the bulged part 100 as the target of resection is larger than the high-frequency electrode 2, the bulged part 100 can not be resected completely in one action and thus the cutting action has to be repeated many times while shifting the flexible sheath 1 a bit forward for each cut and returning it to the original position (incision starting position) after each cut.

However, the flexible sheath 1, being returned to the original position after partially cutting the bulged part 100, tends to get snagged on the bulged part 100. Therefore, the endoscope has to be operated carefully so as to return the flexible sheath I to the original position avoiding the interference by the bulged part 100 and it takes a lot of trouble for precisely setting the flexible sheath 1 at the next incision starting position.

SUMMARY OF THE INVENTION

The present invention is advantageous in that it provides an a high-frequency cutting instrument for an endoscope, which allows an operator of the instrument to perform the mucosal resection treatment (in which the partial horizontal incision of a bulged part of a mucous membrane is repeated many times) with ease and in a short time.

According to an aspect of the invention, there is provided a high-frequency cutting instrument for an endoscope, which is provided with a flexible sheath formed of insulating material, a high-frequency electrode placed to be exposed on a lateral part of the flexible sheath in the vicinity of a tip of the flexible sheath, and a conductive wire inserted into the flexible sheath and electrically connected to the high-frequency electrode. In this structure, the flexible sheath is separated into a distal sheath and a proximal sheath at a separating position along the flexible sheath. The distal sheath and the proximal sheath are connected together at the separating position to be rotatable relative to each other around an axis line of the flexible sheath. Further, the distal sheath is rotated relative to the proximal sheath around the axis line by rotating the conductive wire around the axis line at a proximal end of the proximal sheath.

By the high-frequency cutting instrument for an endoscope composed as above, after each cutting action for partially cutting a bulged part of a mucous membrane, the next cutting action can be started immediately by rotating the high-frequency electrode approximately 180 degrees, by which the mucosal resection treatment (repeating the partial horizontal incision of a bulged part of a mucous membrane many times) can be carried out in a short time and with extreme ease.

Optionally, the separating position may be located in the vicinity of the tip of the flexible sheath and on a proximal side of the high-frequency electrode Still optionally, the high-frequency electrode may be implemented by a linear object which is placed to be exposed to an outside of the distal sheath between a pair of through holes formed through a lateral wall of the distal sheath.

Still optionally, the high-frequency electrode is formed by extending the conductive wire.

Still optionally, the high-frequency electrode may be formed by pulling out the extending part of the conductive wire via a front one of the through holes, folding the extending part backward, and pulling the extending part folded backward into the distal sheath via a rear one of the through holes.

Still optionally, the extending part of the conductive wire pulled into the distal sheath via the rear through hole may be wound around the conductive wire inside the proximal sheath.

Still optionally, the extending part pulled into the distal sheath may be wound around the conductive wire without being firmly fixed to the conductive wire.

In a particular case, the conductive wire may be made of a stranded wire including a straight core wire and a plurality of element wires wound around the core wire, and the high-frequency electrode may be formed by a distal part of the core wire extending from distal ends of the element wires.

Optionally, the distal ends of the element wires may be mechanically fixed to a root of the extending part of the core wire by swaging.

In a particular case, the high-frequency cutting instrument may include an index which is formed at a position on the distal sheath opposite to the high-frequency electrode.

In a particular case, the high-frequency cutting instrument may include an index which is formed at a position shifted linearly from a position opposite to the high-frequency electrode.

Optionally, a proximal end of the distal sheath maybe inserted into a distal end of the proximal sheath to loosely engage with the distal end.

Still optionally, the high-frequency cutting instrument may include a stopper tube which is fixed on the distal sheath to restrict relative movement of the distal sheath and the proximal sheath in a direction of the axis line.

Still optionally, the high-frequency cutting instrument may include a handle connected to the proximal end of the proximal sheath to be held by an operator, and a rotating part connected to a rear end of the conductive wire extending from the proximal end of the proximal sheath to be operated for rotating the conductive wire around the axis line.

Still optionally, the rotating part may be provided with a connection terminal to which a high-frequency power cord for supplying power to the high-frequency electrode is connected.

BRIEF DESCRIPTION OF THE ACCOMPANYING DRAWINGS

The objects and features of the present invention will become more apparent from the consideration of the following detailed description taken in conjunction with the accompanying drawings, in which.

DETAILED DESCRIPTION OF THE EMBODIMENTS

Referring now to the drawings, a description will be given in detail of a preferred embodiment in accordance with the present invention.

In this embodiment, in a high-frequency cutting instrument for an endoscope (comprising a high-frequency electrode placed to be exposed on a lateral part of an electrically insulating flexible sheath in the vicinity of a tip of the flexible sheath and an electrically conductive wire inserted into the flexible sheath and electrically connected to the high-frequency electrode), the flexible sheath is separated into a distal sheath and a proximal sheath at a position in the vicinity of the tip of the flexible sheath and on a proximal side of the high-frequency electrode. The distal sheath and the proximal sheath are connected together at the separating position to be rotatable relative to each other around the axis. The distal sheath is rotated relative to the proximal sheath around the axis by rotating the conductive wire around the axis at the proximal end of the proximal sheath.

Figure 1:
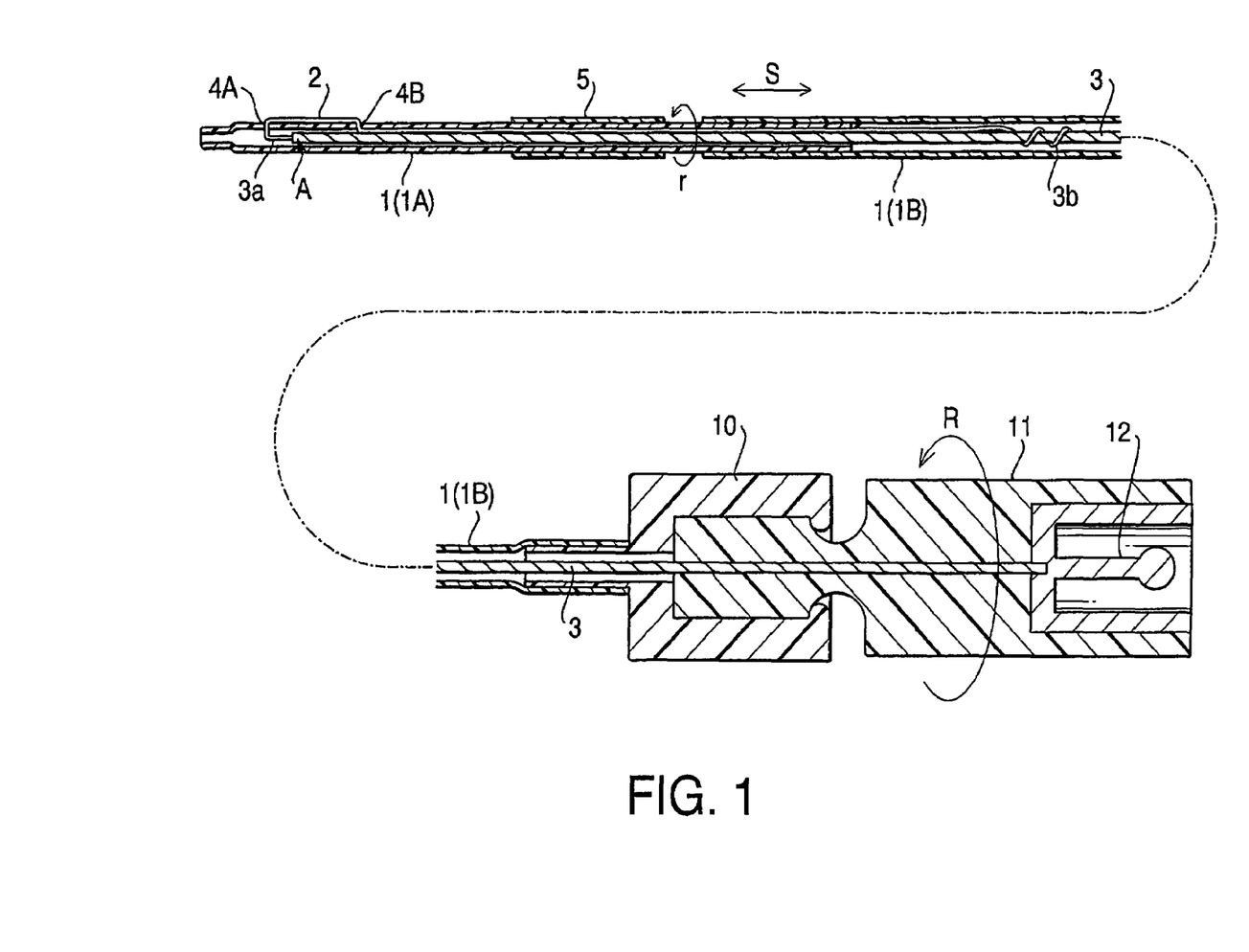
FIG. 1 is a sectional side view showing the overall composition of a high-frequency cutting instrument for an endoscope in accordance with an embodiment of the present invention.

FIG. 1 is a sectional side view showing the overall composition of a high-frequency cutting instrument for an endoscope in accordance with an embodiment of the present invention. In the high-frequency cutting instrument of FIG. 1, a high-frequency electrode 2 is placed to be exposed on a lateral part of an electrically insulating flexible sheath 1 (made of an ethylene tetrafluoride resin tube, for example) in the vicinity of the tip of the sheath 1, and an electrically conductive wire 3 inserted into the flexible sheath 1 is electrically connected to the high-frequency electrode 2.

The flexible sheath 1 is separated into a distal sheath 1A and a proximal sheath 1B at a position in the vicinity of the tip of the flexible sheath 1 and on the proximal side of the high-frequency electrode 2 (e.g. a position 3-10 cm apart from the tip of the flexible sheath 1).

Specifically, the proximal sheath 1B is formed to have an external diameter of approximately 1.5-3 mm and a length of approximately 1-2 m. The distal sheath 1A, having an external diameter suitable for a loose fit in the distal end of the proximal sheath 1B, is inserted approximately 1-2 cm into the proximal sheath 1B, by which the distal sheath 1A is connected to the proximal sheath 1B to be rotatable around the axis of the proximal sheath 1B.

The conductive wire 3 in this embodiment is made of a stranded wire including a straight core wire and a plurality of (5 or 6, for example) element wires wound around the core wire. The high-frequency electrode 2 is formed by a distal part of the core wire protruding and extending from distal ends A of the element wires. The distal ends A of the element wires are mechanically fixed to the root of the extending part 3a of the core wire by swaging. The fixation of the distal ends A of the element wires to the root of the extending part 3a may also be carried out by brazing, etc.

Through a lateral wall of the distal sheath 1A in the vicinity of its tip, through holes 4A and 4B are formed to be apart from each other along the length of the distal sheath 1A. The extending part 3a of the core wire of the conductive wire 3 is pulled out via the front through hole 4A and folded backward. The extending part 3a folded backward is pulled into the distal sheath 1A via the rear through hole 4B. The portion of the extending part 3a of the core wire exposed to the outside of the distal sheath 1A between the pair of through holes 4A and 4B serves as the linear high-frequency electrode 2.

The tip 3b of the extending part 3a of the core wire pulled into the distal sheath 1A via the rear through hole 4B (toward the rear of the distal sheath 1A) passes through the distal sheath 1A and reaches the proximal sheath 1B. The tip 3b of the core wire inside the distal end of the proximal sheath 1B is wound around the conductive wire 3 without being firmly fixed to the conductive wire 3. By such composition, the front end part of the conductive wire 3 is substantially fixed to the distal sheath 1A.

The reference numeral "5" in FIG. 1 denotes a stopper tube which is fixed on the exterior surface of the distal sheath 1A by heat shrinkage, for example. The stopper tube 5 prevents the distal sheath 1A from being pulled inside the proximal sheath 1B when external force S, causing movement of the distal sheath 1A relative to the proximal sheath 1B in the axial direction, is applied. Meanwhile, the conductive wire 3 serves as a stopper for preventing the distal sheath 1A from being pulled out and detached from the proximal sheath 1B.

At a position on the distal sheath 1A directly to the rear of a position opposite to the high-frequency electrode 2, an index is formed. In this embodiment, the index is formed on the stopper tube 5. The index will be explained in detail later referring to FIG. 3.

To the proximal end of the proximal sheath 1B, a handle 10 to be held by the operator is connected. To the rear end of the conductive wire 3 extending from the proximal end of the proximal sheath 1B, a rotating part 11 for rotating the conductive wire 3 around its axis is connected. The rotating part 11 engages with the handle 10 to be freely rotatable around the axis of the conductive wire 3 while preventing its movement in the axial direction.

Both the handle 10 and the rotating part 11 are formed of electrically insulating material. A connection terminal 12, to which an unshown high-frequency power cord can be connected, is provided to the rear end of the rotating part 11 while being connected with the rear end of the conductive wire 3, by which high-frequency electric current can be supplied to the high-frequency electrode 2 via the conductive wire 3.

In the high-frequency cutting instrument (for an endoscope) of this embodiment composed as above, when the operator holding the handle 10 rotates the rotating part 11 around the axis as indicated by the, arrow "R" in FIG. 1, the conductive wire 3 inside the proximal sheath 1B rotates around the axis and the distal sheath 1A also rotates around the axis relative to the proximal sheath 1B as indicated by the arrow "r" in FIG. 1, by which the high-frequency electrode 2 rotates around the axis of the distal sheath 1A.

Figure 2:
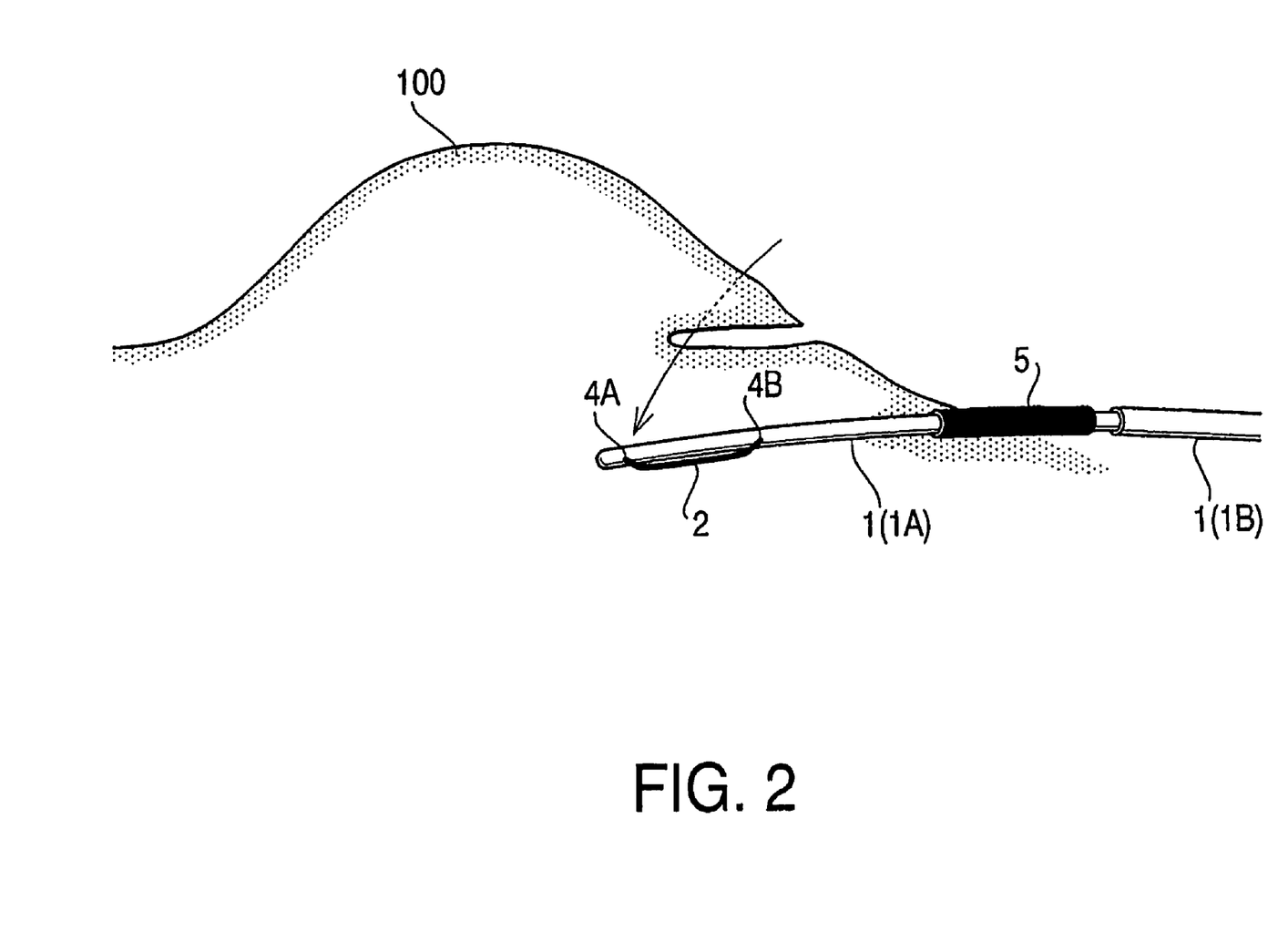
FIG. 2 is a schematic diagram showing mucosal resection treatment employing the high-frequency cutting instrument of the embodiment.

FIGS. 2 through 5 show horizontal incision into a bulged part 100 of a mucous membrane by use of the high-frequency cutting instrument (for an endoscope) of this embodiment. After inserting the flexible sheath 1 into an instrument-inserting channel (unshown) of an endoscope, the rotating part 11 of the high-frequency cutting instrument is turned so that the distal sheath 1A will rotate to let the high-frequency electrode 2 face in a direction suitable for making an incision. Thereafter, high-frequency electric current is passed through the high-frequency electrode 2 and the first horizontal incision is made into the bulged part 100 as shown in FIG. 2 by swinging the proximal sheath 1B.

Figure 3:
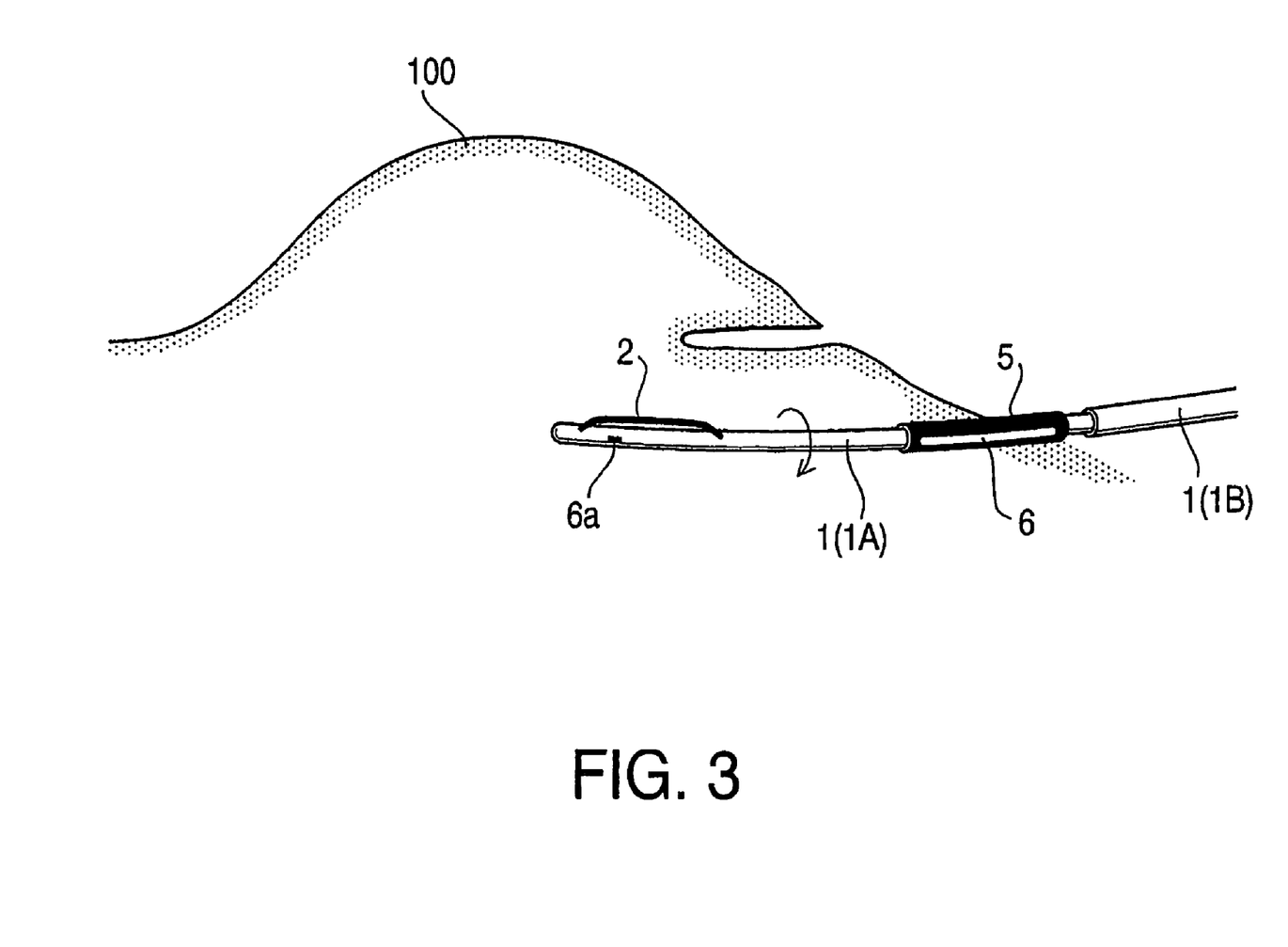
FIG. 3 is a schematic diagram showing mucosal resection treatment employing the high-frequency cutting instrument of the embodiment.

Subsequently, as shown in FIG. 3, the distal sheath 1A is rotated so as to turn the high-frequency electrode 2 approximately 180 degrees, by turning the rotating part 11 at the proximal end of the high-frequency cutting instrument without moving the proximal sheath 1B.

Incidentally, even when the high-frequency electrode 2 which has been turned as above can not be observed through the endoscope, the direction of the high-frequency electrode 2 can be judged correctly by observing the index 6 (formed on the side opposite to the high-frequency electrode 2) through the endoscope.

While the index 6 in this embodiment is formed by removing the surface of the stopper tube 5 (colored black, for example) along a line parallel to the axis of the distal sheath 1A, the index 6 may also be formed in different ways. It is also possible to form an index 6a (as an alternative to the Index 6) at the position (on the exterior surface of the distal sheath 1A) opposite to the high-frequency electrode 2 as shown in FIG. 3.

Figure 4:
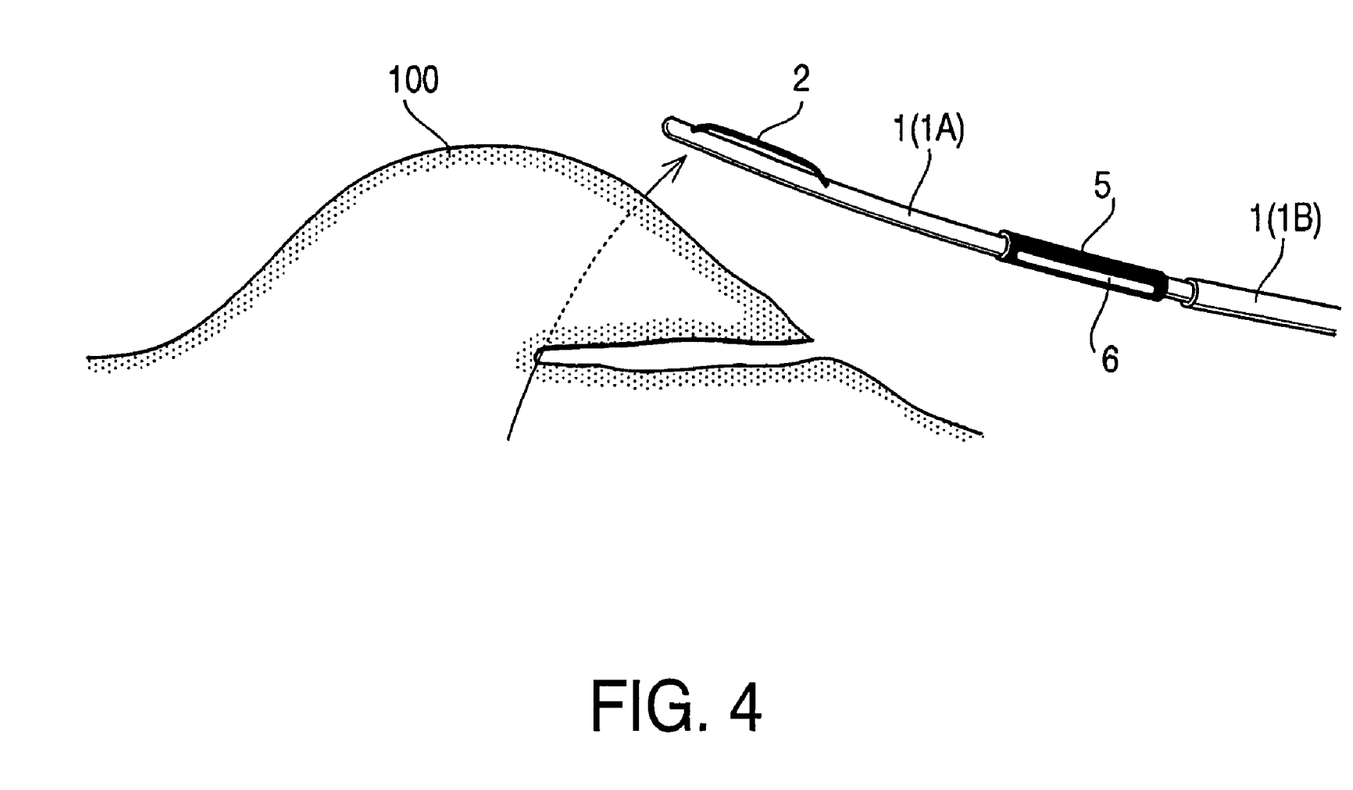
FIG. 4 is a schematic diagram showing mucosal resection treatment employing the high-frequency cutting instrument of the embodiment.

After turning the high-frequency electrode 2 approximately 180 degrees as shown in FIG. 3, the second horizontal incision, extending the first incision, can be made as shown in FIG. 4 by slightly pushing the flexible sheath 1 forward and swinging the flexible sheath 1 in the direction opposite to that in the first incision.

Figure 5:
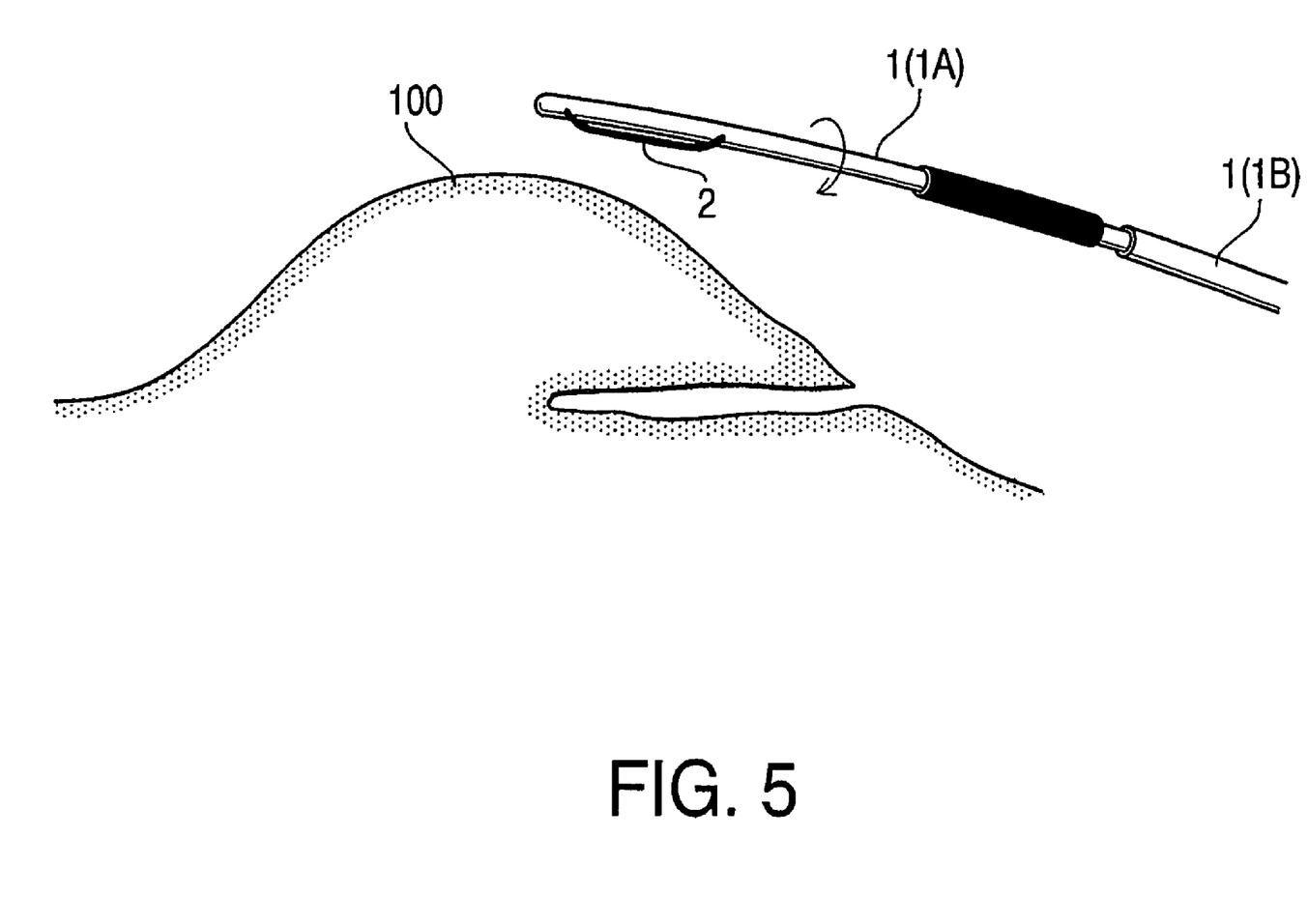
FIG. 5 is a schematic diagram showing mucosal resection treatment employing the high-frequency cutting instrument of the embodiment.

Thereafter, the third and successive horizontal incisions can be made with ease by repeating the reversal of the high-frequency electrode 2 (by approximately 180 degrees) as shown in FIG. 5 by turning the rotating part 11 at the proximal end of the high-frequency cutting instrument.

As described above, according to the embodiment, after each cutting action for partially cutting a bulged part of a mucous membrane, the next cutting action can be started immediately by rotating the high-frequency electrode approximately 180 degrees, by which the mucosal resection treatment (repeating the partial horizontal incision of a bulged part of a mucous membrane many times) can be carried out in a short time and with extreme ease.

While a description has been given above of a preferred embodiment in accordance with the present invention, the present invention is not to be restricted by the particular illustrative embodiment and a variety of modifications, design changes, etc. are possible without departing from the scope and spirit of the present invention described in the appended claims.

For example, while the distal sheath 1A and the proximal sheath 1B are joined together by inserting the distal sheath 1A into the proximal sheath 1B in the above embodiment, it is also possible to employ a connector for rotatably connecting the distal sheath 1A and the proximal sheath 1B, as a component independent of the flexible sheath 1. Similarly, while the high-frequency electrode 2 in the above embodiment is implemented by the exposed portion of the core wire of the conductive wire 3, the high-frequency electrode 2 may also be formed as a component independent of the conductive wire 3.

What is claimed is:

1. A high-frequency cutting instrument for an endoscope, comprising:
   a flexible sheath formed of insulating material;
   a high-frequency electrode placed to be exposed on a lateral part of the flexible sheath adjacent to a tip of the flexible sheath;
   a conductive wire inserted into the flexible sheath and electrically connected to the high-frequency electrode; and
   an index mark which is formed at a position shifted linearly from a position opposite to the high-frequency electrode,
   wherein the flexible sheath is separated into a distal sheath and a proximal sheath at a separating position along the flexible sheath, the distal sheath and the proximal sheath are connected together at the separating position to be rotatable relative to each other around an axis line of the flexible sheath, the distal sheath is rotated relative to the proximal sheath around the axis line by rotating the conductive wire around the axis line at a proximal end of the proximal sheath, and the index mark is formed on the distal sheath and extends linearly in an axial direction of the distal sheath,
   further comprising:
   a handle connected to the proximal end of the proximal sheath to be held by an operator; and
   a rotating part connected to a rear end of the conductive wire extending from the proximal end of the proximal sheath to be operated for rotating the conductive wire around the axis line, the rotating part being provided with a connection terminal to which a high-frequency power cord for supplying power to the high-frequency electrode is connected.

2. The high-frequency cutting instrument according to claim 1,
   wherein the separating position is located adjacent to the tip of the flexible sheath and on a proximal side of the high-frequency electrode.

3. The high-frequency cutting instrument according to claim 1, wherein the high-frequency electrode is implemented by a linear object which is placed to be exposed to an outside of the distal sheath between a pair of through holes formed through a lateral wall of the distal sheath.

4. The high-frequency cutting instrument according to claim 3, wherein the high-frequency electrode is formed by extending the conductive wire to form an extending part.

5. The high-frequency cutting instrument according to claim 4, wherein the high-frequency electrode is formed by pulling out the extending part of the conductive wire via a front one of the through holes, folding the extending part backward, and pulling the extending part folded backward into the distal sheath via a rear one of the through holes.

6. The high-frequency cutting instrument according to claim 5, wherein the extending part of the conductive wire pulled into the distal sheath via the rear through hole is wound around the conductive wire inside the proximal sheath.

7. The high-frequency cutting instrument according to claim 6, wherein the extending part pulled into the distal sheath is wound around the conductive wire without being firmly fixed to the conductive wire.

8. The high-frequency cutting instrument according to claim 4, wherein:

the conductive wire is made of a stranded wire including a straight core wire and a plurality of element wires wound around the core wire, and the high-frequency electrode is formed by a distal part of the core wire extending from distal ends of the plurality of element wires.

9. The high-frequency cutting instrument according to claim 8, wherein the distal ends of the plurality of element wires are mechanically fixed to a root of the extending part of the core wire by swaging.

10. The high-frequency cutting instrument according to claim 1, further comprising an index mark which is formed at a position on the distal sheath opposite to the high-frequency electrode.

11. The high-frequency cutting instrument according to claim 1, wherein a proximal end of the distal sheath is inserted into a distal end of the proximal sheath to loosely engage with the distal end.

12. The high-frequency cutting instrument according to claim 11, further comprising a stopper tube which is fixed on the distal sheath to restrict relative movement of the distal sheath and the proximal sheath in a direction of the axis line.

* * * * *